United States Patent [19]

Schmidbaur et al.

[11] 4,097,509
[45] Jun. 27, 1978

[54] DOUBLE-YLIDE METAL COMPLEXES

[75] Inventors: Hubert Schmidbaur, Garching; Oswald Gasser, Munich, both of Germany

[73] Assignee: Hoechst Aktiengesellschaft, Frankfurt am Main, Germany

[21] Appl. No.: 780,130

[22] Filed: Mar. 22, 1977

[30] Foreign Application Priority Data

Mar. 25, 1976 Germany .............................. 2612644
Jan. 21, 1977 Germany .............................. 2702326

[51] Int. Cl.² ............................................... C07F 1/12
[52] U.S. Cl. .................................. 260/430; 252/431 P; 260/429 R; 260/429 J; 260/439 R; 260/448 A; 260/606.5 P; 260/683.15 D
[58] Field of Search ................. 260/430, 429 R, 429 J, 260/439 R, 606.5 P, 606.5 N, 448 A

[56] References Cited

U.S. PATENT DOCUMENTS 2,998,416  8/1961  Mendel .......................... 252/429 A X
3,686,159  8/1972  Bauer et al. .................... 252/431 P X

OTHER PUBLICATIONS

Schmidbaur et al., Inorg. Chimica Acta 13, pp. 79-83 and 85-89, (1965).
Chemical Abstracts, V83, 193457z, (1975).

Primary Examiner—Helen M. S. Sneed
Attorney, Agent, or Firm—Connolly and Hutz

[57] ABSTRACT

Double-ylide metal complexes are made. To this end, one or more bis-[methyl-(diorganyl)-phosphoranylidene]-methanes of the general formula

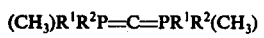

$(CH_3)R^1R^2P=C=PR^1R^2(CH_3)$ in which $R^1$ and $R^2$ each stand independently of one another for an alkyl radical having 1 to 4 carbon atoms, or phenyl or tolyl, are reacted with one or more compounds of a monovalent, bivalent or trivalent metal.

3 Claims, No Drawings

DOUBLE-YLIDE METAL COMPLEXES

This invention relates to double-ylide metal complexes.

The recently synthesized double ylide bis-[trimethylphosphoranylidene]-methane of the formula:

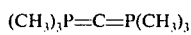

$$(CH_3)_3P=C=P(CH_3)_3 \quad (Ia)$$

(cf. Journal Amer. Chem. Soc. 97 (1975) 6281-2), and its homologues of the formula:

$$(CH_3)R^1R^2P=C=PR^1R^2(CH_3) \quad (I),$$

in which $R^1$ and $R^2$ each stand for an alkyl having 1 to 4 carbon atoms, or phenyl or tolyl, have been tested as to their ligand properties and found to behave ambidentally as shown by the following equation:

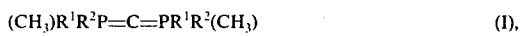

For example, the reaction of 1 mol of bis-diphenylphosphinomethane of the formula $[(C_6H_5)_2-P-CH_2-P-(C_6H_5)_2]$ with more than 2 moles of methyl bromide in tetrahydrofuran at 80° C gives an intermediate product of the formula $Br^-[(C_6H_5)_2CH_3P^+-CH_2-P^+CH_3(C_6H_5)_2]Br^-$, which can be further reacted with an excess of sodium amide with the resultant formation of bis-[methyl-diphenyl-phosphoranylidene]-methane of the formula $(C_6H_5)_2CH_3P=C=PCH_3(C_6H_5)_2$, together with sodium bromide and ammonia.

The above formula "(I)" compounds have unexpectedly been found to be useful components for incorporation in novel chelate systems. More specifically, compounds of the above formula "(I)" can be reacted, for example, with alkyl compounds of certain metals, to give novel double-ylide metal complexes having a variety of technical uses.

The reactions whereby the invention is illustrated and exemplified hereinafter show clearly that either the central C atom of the complex can act as a double donor, or the donor functions can appear in the methyl groups associated therewith, after proton displacement toward the central C atom.

The compound of formula "(Ia)" can be reacted with 2 mols of methyl-(trimethylphosphane) gold (Chem. Ber. 104 (1971), 2829) to produce the novel 1:2 double-ylide complex bis-methyl-gold-bis-trimethylphosphanomethane, 2 mols of trimethylphosphane also being formed. The analytical and spectroscopic data of this complex appear to indicate that it has the formula "(II)" in the following equation:

$$(CH_3)_3P=C=P(CH_3)_3 \text{ (Ia)} + 2 \text{ CH}_3\text{AuP(CH}_3)_3$$

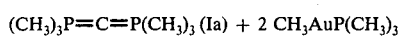

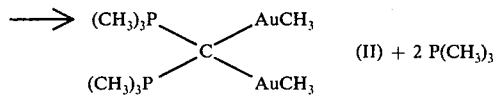

$$(II) + 2 \text{ P(CH}_3)_3$$

The compound of the above formula "(II)" is a colorless substance which is sensitive to air, thermally stable up to 80° C, and soluble in acetone and methylene chloride.

The reaction of the compound of the above formula "(Ia)" with trimethyl gallium in a ratio of 1:1 is accompanied by rapid evolution of methane at temperatures slightly higher than room temperature, and produces the 1:1 double-ylide complex of the formula "(III)" in the following equations:

$$(Ia) + Ga(CH_3)_3 \longrightarrow CH_4 + \quad (III)$$

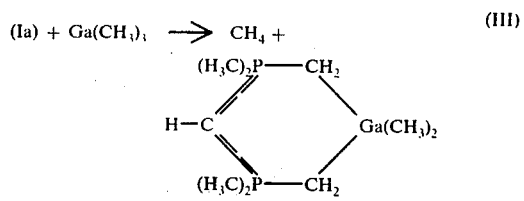

The reaction of zinc or cadmium dialkyl with the compound of the formula (Ia), in which the respective alkane is split off, gives the twice chelatized 2;1 double-ylide complexes "(IVa)" and "(IVb)", respectively, indicated in the following equation:

$$2(Ia) + MR_2 \longrightarrow 2 RH +$$

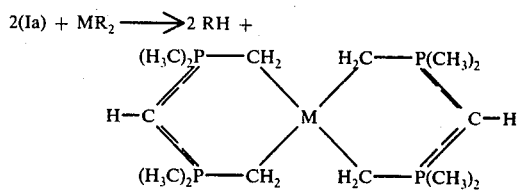

(IVa): M = Zn; R = $CH_3$ or $C_2H_5$.
(IVb): M = Cd; R = $CH_3$ or $C_2H_5$.

The compounds of formulae "(III)", "(IVa)" and "(IVb)" are colorless substances which are readily soluble in organic solvents, e.g., benzene, and are distillable under vacuum; their mass spectra present the molecule peak in the form of an intensive line grouping with corresponding isotopic structures.

The "carbodiphosphoranes" of formula "(I)" afford a widely applicable and efficient ligand system for making stable sigma-organometal double-ylide complexes which are suitable for use as catalysts or co-catalysts in olefin polymerization (cf U.S. Pat. Nos. 2,998,416 and 3,686,159).

The starting materials which may be used for making the present nickel, palladium and platinum complexes include the anhydrous dihalides of these metals, but it may be preferable, for reasons of solubility, to use the corresponding phosphine complexes. The addition of bis-[trimethylphosphoranylidene]-methane to a suspension or solution of these dihalides in an inert solvent initiates a "re-ylidation" reaction, as shown by the following equation, in which methanido-bis-trimethylphosphonium halide is separated and trimethylphosphine may be set free:

$$4 \text{ (CH}_3)_3\text{P=C=P(CH}_3)_3 + [(CH_3)_3P]_2MX_2 \quad (V/VI/VII)$$

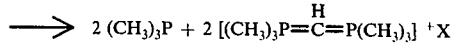

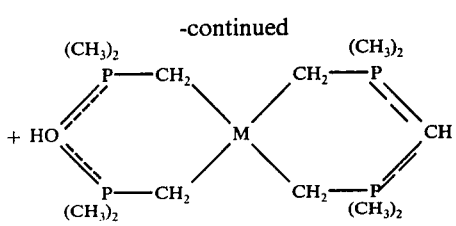

In formula "(V)," M stands for Ni; in formula "(VI)," N stands for Pd; and in formula "(VII)," M stands for Pt. X stands for Cl, Br or I.

The double-ylide complexes of formulae "(V)," "(VI)" and "(VII)," after removal of methanido-bis-trimethyl-phosphonium halide by filtration, can be recovered from the filtrate, to be purified by recrystallization or sublimation. After purification, the compound of formula "(V)" has been obtained in a yield of 65%, but the compounds of formulae "(VI)" and "(VII)" have been obtained in yields as low as 25–28%, due to decomposition accompanied by the precipitation of metal during both the reaction proper and the subsequent work-up. These compounds are yellow to colorless ("(VII)") crystalline substances whose sensitiveness to air and solubility in aprotic organic solvents decreases in the order "(V), " "(VI)," "(VII)." They are readily sublimable under vacuum and thermally stable up to more than 240° C (formula "V" compound) or up to 360° C (formula "VII" compound).

The mass spectra of the complexes of formulae "(V)" to "(VII)" show the molecule ion with the expected isotope distribution and with maximum intensity, so that there is no room for doubt as to the molecule mass. The infrared data indicate clear analogies within the spectral line, and differ only in the region of longer wavelengths, where the metal mass interferes more seriously. In other words, a strong structural relation does evidently exist with respect to the compounds of formulae "(V)" to "(VII)." The structural relationship becomes even more evident in the NMR spectra, which give direct information with respect to the structural units present and their distribution.

In the $\{^1H\}$-$^{31}P$-spectrum, each of the individual compounds produces only one singlet signal; this is reliable evidence of the equivalence of the two chelate units, and of the phosphorus atoms, within each unit. The formula "(VII)" platinum complex shows the $^{31}P$—C—$^{195}Pt$ reciprocal effect which is to be expected and which manifests itself in satellites of the P-signal. This coupling confirms the equivalent covalent linkage of the four $CH_2P$-groups to the central atom.

The $^1H$-spectrum leads to the same conclusion, inasmuch as the $CH_2$-signal observed for the formula "(VII)" compound shows the corresponding satellites of the $^1H$—$C^{195}Pt$-linkage.

These signals, like those of the similarly equivalent $CH_3$ groups, are strongly split up by P-P-reciprocal actions and do appear as $A_2XX'A_2$ or $A_6XX'A'_6$ systems. Despite this, it has been possible to detect some minor linkage of the $CH_3$-hydrogen atoms to the $^{195}Pt$ central atom.

Of particular interest is the resonance of the methanide bridge between the phosphorus atoms, which shows no measurable $^1H$—C—$^{31}P$-linkage but is evidently split up by extensive $^1H$—C—P—C—$^1H$— reciprocal effects. It does not respond to the $\{^{31}P\}$ experiment whereas both the $CH_3$ and $CH_2$ signals collapse into singlets. The resonance surfaces then correspond particularly well to the 12:4:1 ratio required for $CH_3$:$CH_2$:CH.

The results obtained by spectroscopic experiments are fully consistent with the structure postulated. In view of the diamagnetism also evidenced by NMR experiments, it is reasonable to conclude that the two chelate rings are linked to the central atom in such a manner that it is possible for the four $CH_2$ groups to provide a square planar environment.

The gold (III) complexes often exhibit analogous structures to those of the Pt (II) compounds, because of the $d^8$-configuration which is common to them. Subjecting bis-[trimethyl-phosphoranylidene]-methane to reaction with bis-[gold(III)-dimethyl halide] results in the formation of gold dimethyl-[methanido-bis-(dimethyl-phosphonium methylide)] of the following formula (VIII), in accordance with the following equation, methanido-bis-trimethyl-phosphonium halide again being precipitated:

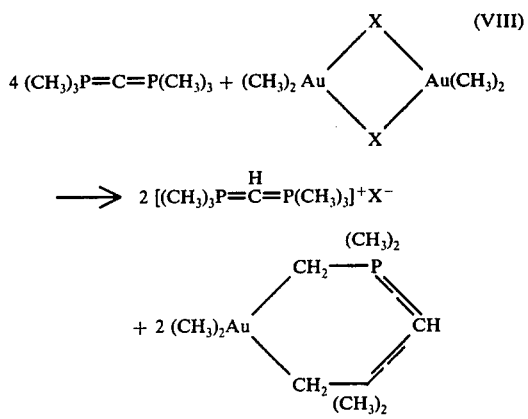

in which X stands for chlorine, bromine or iodine.

The compound of formula (VIII) forms colorless crystals which are only slightly sensitive to air and moisture. The compound of formula (VIII) is readily soluble in organic solvents, and sublimable.

The structure proposed is based on elementary analysis, mass spectrum, $^1H$—, $^1H$— $\{^{31}P\}$ and $^{31}P$ $\{^1H\}$ NMR spectra, and diamagnetism studies.

The present invention provides a process for making a double-ylide metal complex, which comprises reacting (A) one or more bis-[methyl-(diorganyl)-phosphoranylidene]-methanes of the general formula $$(CH_3)R^1R^2P=C=PR^1R^2(CH_3)$$

in which $R^1$ and $R^2$ each stand independently of one another for an alkyl radical having 1 to 4 carbon atoms, or phenyl or tolyl, with (B) one or more compounds of a monovalent, bivalent or trivalent metal, as herein defined. The word "metal" used in the present description and claims is to be understood as including boron.

Preferred features of the present process provide:
(a) for reactant "(A)" to comprise bis-[trimethyl-phosphoranylidene]-methane, this compound having the formula $(CH_3)_3P=C=P(CH_3)_3$;
(b) for reactant "(B)" to comprise one or more compounds of lithium, gold, magnesium, zinc, cadmium, boron, aluminum, gallium, indium, thallium, nickel, palladium or platinum;
(c) for bis-methyl-gold-bis-trimethylphosphanomethane, this compound having the formula

[(CH₃)₃P]₂C(AuCH₃)₂, to be made by reacting bis-[trimethyl-phosphoranylidene]-methane with methyl-(trimethyl-phosphane)-gold, this compound having the formula CH₃AuP(CH₃)₃, in an inert organic solvent at a temperature of −60° to +25° C with the exclusion of air;

(d) for a double ylide complex of the formula

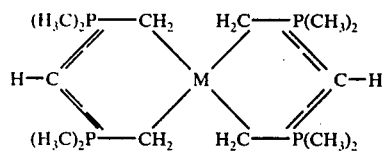

in which M stands for Zn or Cd, to be made by reacting bis-[trimethyl-phosphoranylidene]-methane with a metal dialkyl of the formula MR₂, in which M stands for Zn or Cd, and R stands for CH₃ or C₂H₅, in an inert organic solvent at a temperature of 20° to 110° C;

(e) for a double-ylide complex of the formula

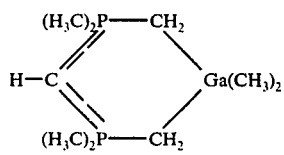

to be made by reacting bis-[trimethyl-phosphoranylidene]-methane with trimethyl gallium or an etherate thereof in an inert organic solvent at a temperature of 20° to 140° C;

(f) for the reactant "(B)" to comprise a compound of the formula MX₂, [(CH₃)₃P]₂MX₂ or [(CH₃)₂AuX]₂, in which formulae M stands for nickel, palladium or platinum, and X stands for chlorine, bromine or iodine;

(g) for a double-ylide complex of the formula:

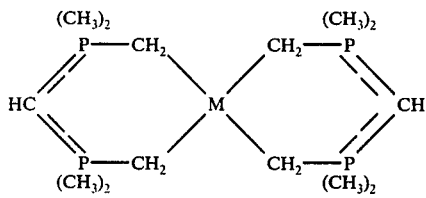

in which M stands for Ni, Pd or Pt, to be made by reacting bis-[trimethyl-phosphoranylidene]-methane with a metal dichloride of the formula MCl₂ or with a compound of the formula [(CH₃)₃P]₂MCl₂ in an inert organic solvent at a temperature of −78° to +80° C with the exclusion of air;

(h) in a process as specified at "(g)" wherein the reactant "(B)" comprises MCl₂, for the reaction to be carried out in the presence of trimethylphosphine as a solubilizing agent;

(i) for a double-ylide complex of the formula

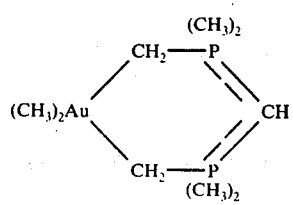

to be made by reacting bis-[trimethyl-phosphoranylidene]-methane with bis-[dimethyl-gold(III) chloride] in an inert organic solvent at a temperature of −78° to +80° C with the exclusion of air; and (j) for the inert organic solvent in "(c)," "(d)," "(e)," "(g)," "(h)" or "(i)" to comprise diethyl ether, benzene, toluene, ortho-, meta- or para- xylene, or cyclohexanol. The invention also includes the following compounds per se:

(k) Bis-methyl-gold-bis-trimethylphosphano-methane of the formula [(CH₃)₃P]₂C(AuCH₃)₂;

(l) A double-ylide metal complex, in the nature of a metal-bis-[methanido-bis-(dimethyl-phosphonium methylide)], of the formula

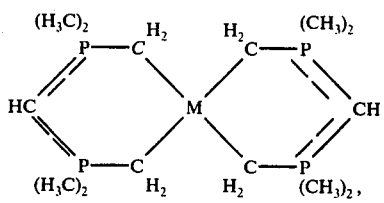

in which M stands for magnesium, zinc, cadmium, nickel, palladium or platinum; and (m) A double-ylide metal complex, in the nature of a dimethyl-metal-[methanido-bis-(dimethyl-phosphonium-methylide)], of the formula

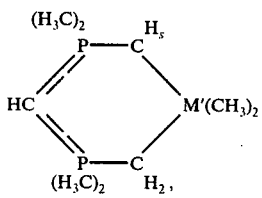

in which M stands for boron, aluminum, gallium, indium, thallium or gold; and their uses as catalysts of cocatalysts in the polymerization of olefins.

The invention thus further includes olefin polymerization processes employing a double-ylide metal complex as specified at "(k)," "(l)" or "(m)," as a catalyst or cocatalyst.

The following Examples illustrate the invention.

EXAMPLE 1

Preparation of bis-methyl-gold-bis-trimethylphosphano-methane (formula "II").

290 mg (1.77 mmol) of the compound of formula "(Ia)," i.e., bis-[trimethyl-phosphoranylidene]-methane, dissolved in 5 ml of ether was added dropwise with agitation, at −60° C, and under dry nitrogen as a protective gas, to a solution of 1.02 g (3.54 mmol) of CH₃AuP(CH₃)₃ in 10 ml of ether. The whole was stirred for 1 hour at 20° C, and the precipitate obtained was thereafter filtered off, washed with n-pentane and dried under vacuum.

The yield was almost quantitative. Melting point: 80° C (decomposition).

$^1$H-NMR (in $CH_2Cl_2$, TMS ext): $\delta CH_3Au$ 0.55 ppm, t, 6H

J(HCAuCP) 1.2 hz. $\delta CH_3P$ 2.34, $A_9XX'A'_9$, 18H, N = 12.2

$^1$H—{$^{31}$P}: s, 6H; s. 18H

Elementary analysis: $C_9H_{24}Au_2P_2$ (588.17): Calculated: C-18.38; H-4.11; Found: C-18.41; H-4.21

EXAMPLE 2

Gallium complex (formula "III")

950 mg (5.8 mmol) of the compound of formula "(Ia)" was introduced into 10 ml of benzene, and the whole was admixed at 20° C with a solution of 1.1 g (5.8 mmol) of gallium trimethyl etherate ($Ga(CH_3)_3 \cdot C_2H_5OC_2H_5$) in 10 ml of benzene. The whole was heated under reflux until methane ceased to be evolved; the solvent was thereafter removed, and the material remaining was distilled under vacuum.

The yield was 80% of the theoretical. Melting point: 41° C.

Determination of molecular weight: 262 ($^{69}$Ga), mass spectrum.

Elementary analysis: $C_9H_{23}GaP_2$ (262.95): Calculated: C-41.11; H-8.82; Found: C-40.38; H-8.80

NMR-spectra:

$^1$H-NMR (in $C_6H_6$, TMS ext): $\delta CH_3Ga$ — 0.35, s. 6H, $\delta CH_2$-0.09, "d," N = 15.8, 4H. $\delta CH$ — 0.53, br.s., 1H $\delta CH_3P$ 0.70, "d," N = 116, 12H $^{31}$P-NMR (in $C_6H_6$, $H_3PO_4$ ext.): $\delta P$ 12.9 s {$^1$H}.

EXAMPLE 3

Zinc complex (formula "IVa").

950 mg (5.8 mmol) of the compound of formula "(Ia)" was introduced into 10 ml of benzene and admixed at 20° C with a solution of 360 mg (2.9 mmol) of diethylzinc in 10 ml of benzene. The whole was heated under reflux until ethane ceased to be evolved, the solvent was removed, and the material remaining was distilled under vacuum.

The yield was 80% of the theoretical.

Melting point: 85° C.

Determination of molecular weight: 390 ($^{64}$Zn), mass spectrum.

Elementary analysis: $C_{14}H_{34}P_4Zn$ (391.69): Calculated: C-42.93; H-8.75; Found: C-42.59; H-8.75

$^1$H-NMR (in $C_6H_6$, TMS ext.): $\delta CH_2$-0.29, "d," N = 13.1, 4H. $\delta CH$-0.36, br.s., 1H $\delta CH_3$ 0.93. "d," N = 11.3, 12H.

$^{31}$P-NMR (in $C_6H_6$, $H_3PO_4$ ext.): P 12.87, s {$^1$H}

EXAMPLE 4

Cadmium complex (formula "IVb").

950 mg (5.8 mmol) of the compound of formula "(Ia)" was introduced into 10 ml of benzene, and the whole was admixed at 20° C with a solution of 400 mg (2.9 mmol) of dimethyl cadmium in 10 ml of benzene. Next, the whole was heated under reflux until methane ceased to be evolved, the solvent was removed, and the material remaining was distilled under vacuum. The yield was 80% of the theoretical. Melting point: 84° C.

Determination of molecular weight: 440 ($^{114}$Cd), MS.

Elementary analysis: $C_{14}H_{34}CdP_4$ (438.72): Calculated: C-38.33; H-7.81; Found: C-38.48; H-7.98

$^1$H-NMR (in $C_6H_6$, TMS. ext.): $\delta CH_3P$ 1.1, d, 12H, $A_6XX'A_6'$,

N = 10.9. $\delta CH_2$ -0.1, d, 4H, $A_2XX'A_2'$, N = 12.0, $^2$I(CdCH) 34.5, $\delta CH$ —0.25, m, 1H.

{$^1$H}-$^{13}$C-NMR (in $C_6D_6$, $C_6D_6$ int. converted to TMS): $\delta CH_3P$ 23.8, m. AXX', N = 61.0. $\delta CH_2$ 2.6 m, AXX'N = 48.8. $\delta CH$ 6.8, t, $^1$I(CH-P) 119.6.

{$^1$H}-$^{31}$P-NMR (in $C_6H_6$, $H_3PO_4$ ext.) 13.2, s. $^2$I(CdCP) 48.0.

EXAMPLE 5

Nickel-bis[methanido-bis(dimethyl-phosphonium-methylide)] (formula "V").

A suspension of 360 mg (1.28 mmol) of bis-(trimethyl-phosphine)-nickel dichloride [$(CH_3)_3P]_2NiCl_2$ in 5 ml of benzene was gradually admixed, with thorough agitation, under nitrogen as a protective gas, with a solution of 840 mg (5.11 mmol) of $(CH_3)_3P=C=P(CH_3)_3$ in 8 ml of benzene. A voluminous colorless precipitate of methanido-bis-trimethyl-phosphonium chloride was obtained, which was stirred for a further 5 hours at 20° C, filtered off under protective gas and washed twice, each time with 5 ml of benzene. The filtrate was freed under vacuum from the trimethylphosphine which was set free, and from solvent. The residue was sublimed at 110° C under a pressure of $10^{-4}$ mm Hg. The yield was 320 mg (65% of the theoretical) of the above formula "V" compound. It was a yellow product. Melting point: 175° C. Decomposition temperature: 240° C.

$C_{14}H_{34}NiP_4$ (385.03): Calculated: C-43.67; H-8.90; Ni-15.25; Found: C-43.77; H-9.00; Ni-14.79

Molar mass: 384 (mass spectrum, $^{58}$Ni).

EXAMPLE 6

Palladium-bis[methanido-bis(dimethyl-phosphonium-methylide)] (formula "(VI)").

290 mg (2.73 mmol) of anhydrous $PdCl_2$, 0.5 ml of trimethylphosphine as a solubilizing agent and 1.79 g (10.90 mmol) of $(CH_3)_3P=C=P(CH_3)_3$ were reacted in the manner described in Example 5. 300 mg of the formula "(VI)" compound was obtained in the form of a pale yellow product. The yield was 25% of the theoretical.

Melting point: 193° C. Decomposition temperature: 245° C. Sublimation temperature: 140° C/$10^{-4}$ mm Hg $C_{14}H_{34}PdP_4$ (432.72): Calculated: C-38,86; H-7.92; Pd-24.59; Found:C-39.22; H-8.12; Pd-23.60

Molar mass: 432 (mass spectrum, $^{106}$Pd)

EXAMPLE 7

Platinum-bis[methanido-bis(dimethyl-phosphonium-methylide)] (formula "(VII)").

150 mg (3.59 mmol) of cis-bis-(trimethylphosphine)-platinum dichloride [$(CH_3)_3P]_2PtCl_2$ and 2.35 g (14.35 mmol) of $(CH_3)_3P=C=P(CH_3)_3$ were reacted in the manner described in Example 5. 520 mg of the formula "(VII)" compound was obtained in the form of a colorless product. The yield was 28% of the theoretical. Melting point: 238° C. Decomposition temperature: about 360° C. Sublimation temperature: 140° C/$10^{-4}$ mm Hg.

$C_{14}H_{34}PtP_4$ (521.41): Calculated: C-32.25; H-6.57; Found: C-32.53; H-6.57

Molar mass: 521 (mass spectrum, $^{195}$Pt).

EXAMPLE 8

Dimethyl gold-[methanido-bis-(dimethylphosphonium-methylide)] (formula "(VIII)").

270 mg (0.51 mmol) of bis[dimethyl gold(III)-chloride]and 340 mg (2.06 mmol) of $(CH_3)_3P=C=P(CH_3)_3$ were reacted in the manner described in Example 5. 250 mg of the formula "(VIII)" compound was obtained in the form of a colorless product. The yield was 64% of the theoretical. Melting point: 106° C. Decomposition temperature: about 325° C. Sublimation temperature: 115° C/10$^{-4}$ mm Hg.

$C_9H_{23}AuP_2$ (390.20): Calculated: C-27.70; H-5.94; Au 50.48; Found: C-27.69; H-5.97; Au 50.19
Molar mass: 390 (mass spectrum).

The following Table sets forth NMR data for the double-ylide complexes of formulae "(V)" to "(VIII)."

TABLE

| Formula: | V | VI | VII | VIII |
|---|---|---|---|---|
| $^1H$ | | | | |
| δCH$_3$P | 1.54 | 1.34 | 1.31 | 0.99 |
| I(HCP) | 11.3 | 10.9 | 10.9 | 11.25 |
| I(HCPCM) | — | — | 3.0 | — |
| δCH$_2$P | −0.12 | 0.41 | 0.96 | 0.77 |
| I(HCP) | 15.4 | 12.4 | 12.0 | 13.5 |
| I(HCM) | — | — | 71.3 | — |
| δCHP | 0.23 | −0.04 | −0.34 | −0.33 |
| δCH$_3$M | — | — | — | 1.01 |
| $^{31}P$ | | | | |
| δP | 10.2 | 10.7 | 11.2 | 13.8 |
| I(PCM) | — | — | 136.0 | — |

All compounds were dissolved in benzene and tested at 35° C; the rel. ext. TMS or H$_3$PO$_4$ δ-data are in ppm, the I-values in hz. For the sake of simplicity the "I(HCP) value" is here indicated as N=[I(HCP) + I(HCPCP)] for the present (AnX)$_2$-spin system (n = 2.3).

We claim:
1. Bis-methyl-gold-bis-trimethylphosphano-methane of the formula: $[(CH_3)_3P]_2C(AuCH_3)_2$.
2. A double-ylide metal complex of the formula

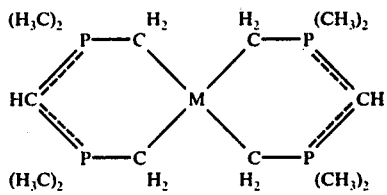

in which M stands for magnesium, zinc, cadmium, nickel, palladium or platinum.

3. A double-ylide metal complex of the formula:

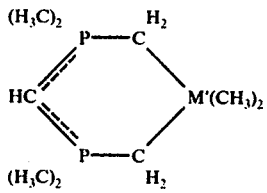

in which M' stands for boron, aluminum, gallium, indium, thallium or gold.

* * * * *